United States Patent [19]

Mencacci

[11] 4,179,986
[45] Dec. 25, 1979

[54] LOW LIQUID VOLUME RETORT SYSTEM

[75] Inventor: Samuel A. Mencacci, San Jose, Calif.

[73] Assignee: FMC Corporation, San Jose, Calif.

[21] Appl. No.: 751,923

[22] Filed: Dec. 16, 1976

[51] Int. Cl.² ............................ A23L 3/02; A23L 3/10
[52] U.S. Cl. ...................................... 99/359; 426/232; 126/369
[58] Field of Search .......... 99/359, 360, 366, 370-371, 99/403-404, 409, 467-470; 426/232, 405, 407, 412; 220/10; 128/220; 137/206; 285/24

[56] References Cited

U.S. PATENT DOCUMENTS

| 539,124 | 5/1895 | Empson | 99/366 |
|---|---|---|---|
| 2,082,460 | 6/1937 | Omsted | 99/370 |
| 2,374,425 | 4/1945 | DeWeerth | 99/360 X |
| 3,026,885 | 3/1962 | Eytinge | 99/405 X |
| 3,480,451 | 11/1969 | Hardison | 99/359 |
| 3,511,169 | 5/1970 | Fritzberg et al. | 99/370 |
| 3,531,300 | 9/1970 | Greenberg et al. | 426/232 |
| 3,592,668 | 3/1968 | Denk | 99/330 |
| 3,613,550 | 10/1971 | Thompson | 99/330 |
| 3,733,202 | 5/1973 | Marmor | 99/404 X |
| 3,824,917 | 7/1974 | Kawahara et al. | 99/404 |

FOREIGN PATENT DOCUMENTS

| 480028 | 4/1927 | Fed. Rep. of Germany | 99/359 |
|---|---|---|---|
| 557214 | 2/1932 | Fed. Rep. of Germany | 99/359 |
| 744791 | 3/1943 | Fed. Rep. of Germany | 99/359 |

*Primary Examiner*—Harvey C. Hornsby
*Assistant Examiner*—Arthur O. Henderson
*Attorney, Agent, or Firm*—A. J. Moore; C. E. Tripp

[57] ABSTRACT

A low liquid volume retort system is provided with a tunnel disposed within and spaced from the side walls and cover of a retort. A plurality of spaced containers are loaded in the tunnel, and a liquid maintained at a temperature different from that of the containers is then pumped from an inlet end of the tunnel to the outlet end to completely fill the tunnel and to evenly transfer heat between all of the containers and the liquid. The liquid then overflows from the outlet end of the tunnel and gravitates to the lower portion of the retort for return to a desired processing temperature and recirculation through the tunnel. The quantity of liquid required for processing is greatly reduced by filling only the tunnel with liquid, and collecting only a small portion of the liquid at the bottom of the retort before again recirculating the liquid through the tunnel and past the containers therein being processed.

13 Claims, 7 Drawing Figures

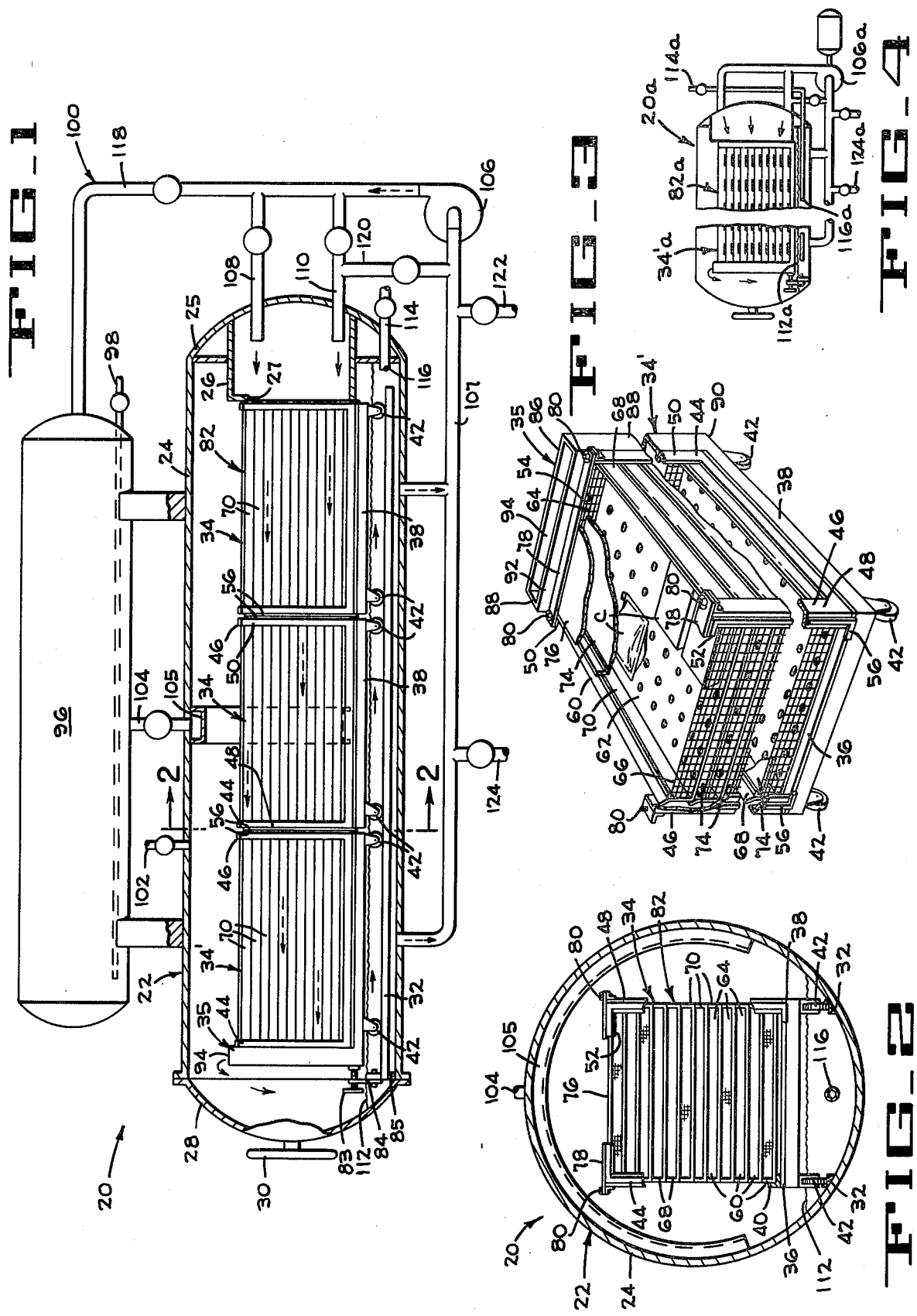

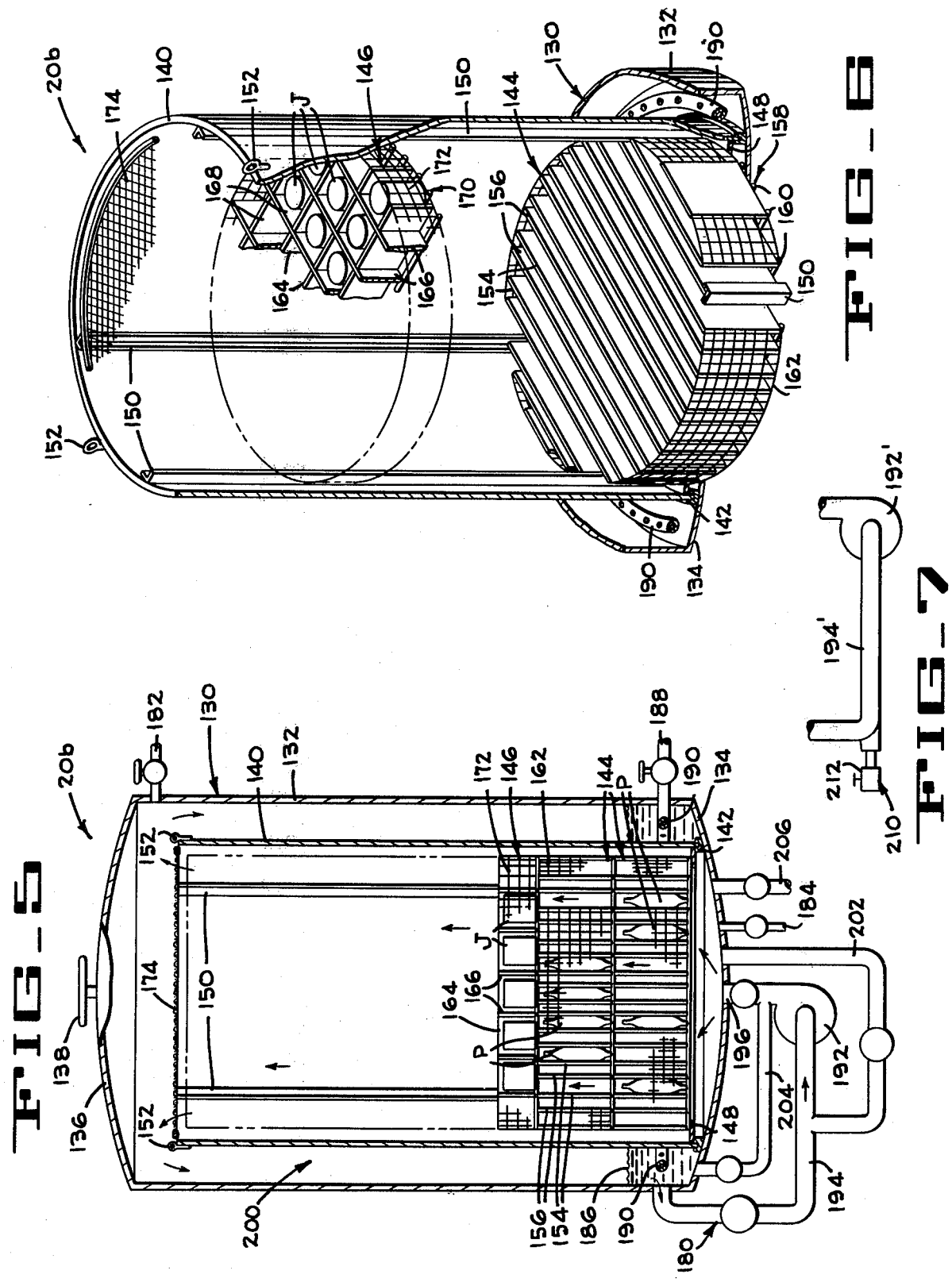

LOW LIQUID VOLUME RETORT SYSTEM

CROSS REFERENCE TO RELATED APPLICATION

This application is an improvement to the retort system and method disclosed in U.S. Mencacci et al application Ser. No. 522,067 filed on Nov. 8, 1974 which issued on Jan. 18, 1977 as U.S. Pat. No. 4,003,302. The subject matter of the Mencacci et al application is incorporated by reference herein.

BACKGROUND OF THE INVENTION

1. Field of the Invention

This invention pertains to retort systems for heat treating containers, and more particularly relates to a system for evenly and efficiently heating or cooling all containers in a batch of containers while using a minimum of heat treatment liquid.

2. Description of the Prior Art

In general, prior art retort systems receive batches of containers, such as filled cans, jars, pouches or trays, which are first heated in hot water until sterilized and are thereafter cooled by cold water. In order to prevent damage to the containers when the pressure within the containers tends to exceed the pressure externally of the containers, an overriding air pressure is usually applied over the water in these prior art devices. The water in the pressure vessel or retort is usually caused to either cascade down upon the flat upper ends of the containers, or alternately is moved horizontally against the rounded surfaces of the upstream containers with little regard to whether or not the other containers in the batch of containers being processed, and especially those near the middle of the batch, receive the same amount of heat as the upper or outer containers.

The problem of providing uniform heat to each container has been solved by the method disclosed in the above mentioned Mencacci et al application of which I am a co-inventor and which application is assigned to the assignee of the present invention. In the Mencacci et al device, containers are loaded into a tunnel within a closed retort and water is then circulated from one end to the other of the retort, which other end opens directly into the retort. In order to assure that the uppermost containers in the tunnel are completely immersed in flowing water, the water in the Mencacci et al retort, both within and externally of the tunnel, is maintained at a level above the tunnel. Thus, when changing from the cooking to the cooling cycle of operation, a very large amount of hot water externally of the tunnel must either be stored in a very large and expensive storage tank, or must be drained and thereafter cold water must be reheated for the next batch of containers with a substantial loss in heating energy.

U.S. Pat. No. 3,776,257 which issued to Piegza on Dec. 4, 1973 discloses a high pressure retort system with flat walls which separate an article and liquid filled heat treatment chamber from the outer curved area of the retort thereby reducing the amount of liquid processing medium required. A gas pressure is applied to the external surfaces of the flat walls to prevent pressure induced bowing of the flat walls.

Greenberg et al U.S. Pat. No. 3,531,300 which issued on Sept. 29, 1970; and similar Katz et al U.S. Pat. No. 3,769,028 which issued on Oct. 30, 1973 both disclose a vertically oriented pressure vessel which uses a propeller for imparting a circulating movement to a heat transfer medium such as water, steam, or hot air. The containers being processed are illustrated as being pouches that are mounted in trays. However, neither of these patents disclose the use of a tunnel within which the batch of containers are evenly heat treated by virtue of a liquid moving into an inlet end of the tunnel and out the other end for return to the inlet end externally of the tunnel.

SUMMARY OF THE INVENTION

The low liquid volume retort system of the present invention includes a pressure vessel having a tunnel therein for accommodating batches of containers. If the tunnel is disposed horizontally, one or more carts filled with containers are used to form a substantially liquid tight tunnel. The heat treatment liquid is directed into one end of the tunnel, flows horizontally past all containers, and then enters an overflow housing which closes the discharge end of the tunnel except for an overflow opening disposed above the level of the containers in the tunnel The heat treatment liquid discharged from the overflow opening is accumulated in the bottom of the pressure vessel below the tunnel. When in the cooking cycle, a shallow pool of the hot overflow liquid is reheated while in the bottom of the pressure vessel (or by direct steam injection into the pump lines) and is recirculated through the tunnel by a pump thus using very little liquid in excess of that required within the tunnel. If it is desired to save this small amount of heated liquid as well as the liquid within the tunnel during the cooling cycle to minimize the cost of heating, a much smaller storage tank is required as compared to that required by said Mencacci et al system. Alternatively, the equipment owner may desire to merely drain the small amount of excess hot water and the water within the tunnel thus eliminating the need for a pressure storage tank at the expense of a slightly higher heating cost.

If the pressure vessel and tunnel are oriented vertically, the containers are loaded into trays stacked within a tunnel that is cylindrical and is substantially sealed to the pressure vessel at its lower end. A pump circulates the heat treatment liquid upwardly through the tunnel causing the liquid to overflow from the open upper end of the tunnel for collection in a shallow annular pool in the lower end of the vessel externally of the tunnel. At the option of the equipment owner, the small amount of excess hot liquid and the hot liquid within the tunnel may either be collected in a small annular storage area within the vessel and externally of the tunnel or in a small storage tank externally of the vessel; or all of the hot liquid may be drained from the system after the cooking step and prior to the cooling step.

It is therefore an object of the present invention to provide an improved retort system and method for evenly treating a submerged batch of containers with heat treatment liquid while using a minimum of liquid.

BRIEF DESCRIPTION OF THE DRAWINGS

FIG. 1 is a diagrammatic elevation of the first embodiment of the retort system of the present invention illustrating a horizontal retort shown in vertical central section with a hot water holding tank thereabove.

FIG. 2 is a vertical section taken along lines 2—2 of FIG. 1 illustrating one end portion of an intermediate cart of said system.

FIG. 3 is a perspective with parts broken away of the outlet end cart of the tunnel of carts illustrated in FIG. 1.

FIG. 4 diagrammatically illustrates a small single cart retort system which does not require a hot water holding tank.

FIG. 5 is a vertical section of a modified retort system having a vertically oriented pressure vessel and tunnel therein, said system further illustrating trays stacked therein which are adapted to handle two different types of containers.

FIG. 6 is a perspective of the tunnel and trays of FIG. 5 illustrating the structure for mounting the tunnel in the vessel and the trays in the tunnel.

FIG. 7 is an elevation of a recirculating pump and steam injector for heating the water circulated through the system during the cooking cycle.

DESCRIPTION OF THE PREFERRED EMBODIMENT

The horizontal retort system 20 (FIGS. 1 and 2) of the first embodiment of the invention comprises an elongated retort or pressure vessel 22 having a cylindrical body 24 with one end closed by an end wall 25. A water inlet passage 26 is secured to the end wall 25 and has a rectangular outlet opening 27. The other end of the body 24 is selectively opened and closed by a door 28 pivoted to said other end and sealed in pressure tight engagement therewith in a well known manner with the aid of a hand operated latch 30.

A pair of angle or channel tracks 32 are secured to the lower portion of the pressure vessel 22 and serve to support one or more container supporting carts 34. The carts 34 are similar to those disclosed in the aforementioned Mencacci et al application except that the end cart 34' includes an overflow housing 35.

Each cart 34 and 34' includes an imperforate bottom plate 36 secured to a generally horizontal frame 38 with a pair of spaced horizontal angle bars 40 (only one being shown in FIG. 2) secured to the upper longitudinal edges of the plate 36. Four wheels 42 are journaled on the frame 38 and are adapted to be supported by the aforementioned tracks 32. Two upstanding peripheral end frames 44 and 46 are formed by pairs of spaced angle posts 48,50 rigidly secured to the frame 38, and having their upper ends interconnected by bars 52 and 54, respectively, to provide rectangular flow passages therethrough. Resilient rubber or plastic peripheral sealing strips 56 of generally rectangular configuration and of the same size as the flow passages are secured to the outer ends of each cart end wall 44,46, and when adjacent strips 56 are moved into abutting contact define a substantially water tight seal.

A plurality of nesting trays 60 are filled with containers C to be treated. As indicated in FIG. 3, the containers may be pouches, trays, glass jars, and cans or the like. The longitudinal edges of the lowermost tray 60 are supported on the angle bars 40 (FIG. 2) to provide a flow passage between the lower tray and the imperforate bottom plate 36. Each tray includes a perforated bottom wall 62; perforated end wall 64,66 of expanded metal, screening or the like; and solid side walls 68,70. After each tray is loaded with containers C, the trays are placed in the cart 34 (or 34') in nesting relationship, with the corners of the trays guided by the angle posts 48,50. Chevron type peripheral seals (not shown) may be secured to the inner surfaces of the two peripheral end frames 44,46 in substantial alignment with the peripheral sealing strip 56 to seal the trays to the peripheral end frames 44,46.

After the filled trays 60 have been loaded into the carts 34,34'; a U-shaped perforated hold down plate or screen 74 is placed in each tray including the uppermost tray to define a water flow passage on each side of each row of containers C. An imperforate cover plate 76 is placed over the plate or screen 74 to provide an additional flow passage therebetween. If the containers being processed are pouches, the hold down plate 74 and the bottom 62 of each tray are preferably imperforate. If other types of containers are being processed, the hold down plate 74 and bottom 62 may be perforated if desired.

The cover plate 76 which may be provided with a resilient sealing strip (not shown) adjacent its lower peripheral edge, is clamped against the top tray by straps 78 and cooperating bolts 80. Thus, the imperforate cover plate 76, the imperforate bottom plate 36, and the nesting side walls 68,70 of the trays cooperate to define a segment of a heat treatment tunnel 82 which is sealed to other tunnel segments and to the rectangular outlet opening 27 of the water inlet passage by the resilient sealing strips 56 when the multiple cart system of FIG. 1 is being used.

The several carts 34,34' are held together and in sealing engagement with the outlet opening 27 by any suitable means such as a hand screw 83 threaded into a lever 84 that is pivotally mounted on a bracket 85 of the pressure vessel for movement between the illustrated locking position in the path of movement of the carts and a position disposed below the path of movement of the carts.

As indicated in FIG. 1, all the carts are identical except for the end cart 34' (or the single cart in the one cart system illustrated in FIG. 4). The end cart 34' is identical to the carts 34 except that the previously mentioned overflow housing 35 is rigidly secured to the end frame 44 in fluid tight engagement. The overflow housing 35 includes a closed end wall 86, a pair of side walls 88, a short bottom wall 90, and an intermediate wall 92 having a larger rectangular fluid flow aperture therein that registers with the flow apertures in the cart end wall 44 as best illustrated in FIG. 3. The upper end of the housing 35 has an overflow port 94 therein that extends above the upper level of the tunnel 82. Thus, water circulated through the tunnel 82 must completely fill all voids in the tunnel since the water is discharged from the overflow port 94 which is at an elevation higher than that of the uppermost portion of the tunnel.

It will be noted that in the multiple cart retort system 20 as illustrated in FIG. 1, a relatively small capacity storage tank 96 is provided to receive and store hot water after the cooking cycle has been completed and before the cooling cycle begins. A valved steam distribution pipe 98 is disposed within the tank 96 to maintain the water therein at the desired cooking temperature of approximately 250° F.

The operation of the multiple cart system of FIG. 1 will be described in conjunction with the fluid control and circulation system 100 for the processing fluids. Since the control system for the multiple cart retort 20 as illustrated in FIG. 1 is substantially the same as that disclosed in the aforementioned Mencacci et al application, such control and circulation system 100 will only briefly be described.

After the pressure vessel 22 has been loaded with carts 34,34' filled with container C to be processed and after the door has been closed, a high pressure gas such as air or a steam-air mixture is directed into the closed pressure vessel 22 through a valved conduit 102 until the pressure within the vessel reaches about 20 psi gauge. Hot water at about 250° F. is then directed into the vessel from the supply tank 96 through valved conduit 104. An arcuate channel deflector 105 is secured to the inner surface of the upper portion of the cylindrical body 24 of the pressure vessel 22 to deflect water away from the top of the tunnel 82 so that it will flow directly into the bottom of the pressure vessel. It is also apparent that a pump and external conduit system (not shown) may be connected between the storage tank 96 and the bottom of the pressure vessel 22 if more rapid filling of the vessel is desired.

A pump 106 is then started, drawing the hot water through conduit 107 from the lower portion of the vessel 22 and circulating it through valved conduits 108 and 110 into and through the inlet passage 26 and tunnel 82 and out of the overflow port 94. This water is collected in a shallow pool 112 in the lower portion of the pressure vessel 22, is reheated by steam from a valved conduit 114 and an attached perforated steam pipe 116 (only a fragment being shown), and is continuously circulated through the tunnel 82 until the particular food product being processed has been cooked and sterilized.

After the product has been cooked, the valved conduits 108 and 110 are closed and the hot water is pumped from the bottom of the vessel 22 into the supply tank 96 through a valved conduit 118 while pressure within the vessel is maintained at about 20 psi gauge to prevent bursting of the containers. During this time, the hot water within the tunnel may also be pumped into the tank, if desired, by opening a valved bypass conduit 120. After the hot water has been drained from the tunnel 82, and the valved conduits 118 and 120 have been closed, the retort system 20 is prepared for the cooling phase of its operation.

Cooling water is then directed into the inlet of the pump 106 through valved water conduit 122 and the valved conduits 108 and 110 which are opened thereby causing the cooling water to circulate through the tunnel 82 and out of the overflow port 94 for recirculation. During cooling a portion of the cooling water, which is heated by the hot containers, is drained from the system through a valved drain conduit 124. As the containers and contents are being cooled to below the boiling point of water at atmospheric pressure, the pressure within the vessel 22 is gradually reduced to atmospheric pressure. The cooling water is then drained from the system by fully opening valved drain conduit 124 and the valved bypass conduit 120. The door 28 of the pressure vessel 20 is then opened, the processed carts 34' and 34 are removed from the vessel after first releasing and dropping the hand screw 83 below the carts. A new batch of containers in the carts are then moved into and locked within the pressure vessel, and the process is repeated as above described.

Although the above process has been described as including the step of storing hot water in the tank 96 during the cooling operation, it will be appreciated that the hot water need not be stored but may be drained from the system if desired. If the hot water is not to be stored, it is apparent that the overall initial cost of the system is substantially reduced since a supply tank capable of storing water under pressure is not required.

FIG. 4 illustrates one such low cost system with a single cart 34'a and no water supply tank. It will be understood that the operation is the same as that described above except that during the start of the cooking cycle, the water entering the vessel is cold water and must be heated to cooking temperature in the shallow pool 112a in the lower portion of the vessel 20a by steam from the valved steam conduit 114a and steam pipe 116a. After the cooking step has been completed, most of the hot water is drained from the bottom of the vessel and from the tunnel 82a through the pump 106a by opening the drain conduit 124a. It will be noted that the pump will not be operating at this time and that the hot water in the tunnel will pass in a reverse direction through the pump 106a before passing out of the valved drain conduit 124a. As in the first embodiment, pressure in the vessel will be maintained at about 20 psig until the cooling cycle is commenced and the temperature of the product within the containers is reduced to below about 212° F.

A vertically oriented retort system 20b of the present invention is illustrated in FIGS. 5 and 6 and constitutes a third embodiment of the invention. The retort system 20b comprises a pressure vessel 130 including a vertical cylindrical housing wall 132, a lower concave end wall 134 and a door 136 pivoted to the upper end of the cylindrical wall 132 and movable between an open position and a closed position. A manually operated hand wheel 138 is provided to lock the door in pressure tight engagement with the cylindrical wall 132 in a well known manner.

An open ended cylindrical tunnel 140 is preferably rigidly secured within and sealed to the concave lower wall 134 by an annulus 142 having a groove and rubber seal (not shown) for receiving the lower end of the tunnel 140.

A plurality of container supporting trays 144 for receiving flat containers such as pouches P; or trays 146 for receiving cylindrical containers such as cylindrical cans or jars J, are stacked in the tunnel 140 either by hand or with the aid of a crane depending upon the size and weight of the trays. The periphery of the lowermost tray 144 or 146 is supported by a ring 148 secured as by welding to the lower end portion of the tunnel 140. A plurality of vertical angle bars 150 are secured to inner walls of the tunnel and serve to retain the several trays in desired angular relationship to each other.

Although the tunnel 140 is preferably rigidly secured within the vessel 130, it will be understood that the tunnel may be sealed, but not secured, to the annulus 142 so that the tunnel and loaded trays may be lowered into or raised from the vessel 130 as a unit. In this way the trays may be loaded into and be unloaded from the tunnel 140 at a point remote from the vessel. This will permit preloading of other tunnels with filled trays for more quickly performing the unloading and loading operations. A crane with the aid of I-bolts 152 secured to the tunnel 140 may be used with this alternate embodiment of the invention.

Each pouch accommodating tray 144 comprises spaced pairs of spaced vertically extending plates 154,156 between which the pouches P are supported with the longitudinal axes vertical as indicated in FIG. 5. The lower edges of the plates are welded to a perforated floor 158 illustrated in the drawings as spaced bars 160. A generally cylindrical screen 162 is mounted around a major portion of the generally circular periphery of the tray 144 and is welded to the floor 158 as well as to the ends of the plates 154,156 to retain the pouches therein. Each cylindrical jar or can tray 146 comprises a plurality of vertical plates 164,166 disposed at right angles to each other to define pockets 168 therein for accommodating individual containers. The plates 164,166 are welded together and to a perforated floor 170 and a peripheral screen 172. A screen 174 is disposed above the uppermost tray of containers to prevent flotation of the containers.

The operation of the vertical retort system 20b will be described in conjunction with a fluid control and circulation system 180 (FIG. 5) for the processing fluids.

The tunnel 140 is first loaded with trays 144 or 146 with filled containers therein, and then the door 136 is closed and locked in pressure tight engagement. A high pressure gas such as air or a steam-air mixture is then directed into the pressure vessel 130 through a valved air conduit 182 until the pressure is raised to about 20 psi gauge. A heat treatment liquid such as water is then directed into the tunnel through a valved water conduit 184 until the tunnel 140 is filled with water and overflows to form a shallow pool 186 of water in the bottom of the vessel. Steam is then introduced into the pool 186 through a valved steam conduit 188 and a perforated annular steam distribution pipe 190 to heat the water to about 250° F. A pump 192 is then started and circulates the hot water from the pool 186 through a valved suction conduit 194, a valved inlet conduit 196, and the tunnel 140. The water overflowing from the top of the tunnel is reheated and recirculated until the product within the containers has been sterilized and is cooked to the desired amount thus completing the cooking cycle.

While maintaining the 20 psig overriding air pressure within the vessel, the majority of hot water is pumped out of the tunnel 140 and into the annular chamber 200 between the tunnel and the cylindrical housing wall 132 for storage. In order to store the hot water, the valved suction conduit 194 and the valved inlet conduit 196 are closed, while a valved storage suction conduit 202 and a valved storage inlet conduit 204 are opened. The pump draws the hot water from the tunnel 140 and stores it in the annular chamber 200 for use during the next cooking cycle of the next batch of containers. The valved conduits 202 and 204 are then closed and cold water is directed into the tunnel 140 through the valved water conduit 184 until the water rises to a level above the uppermost containers in the tunnel 140. After the tunnel is filled with cooling water, a valved drain conduit 206 is partially opened to maintain circulation of the cold water until the containers and their contents are cooled to a temperature below the boiling point of water at atmospheric pressure. The valved water inlet conduit 184 is then closed, all of the cooling water is drained from the tunnel 140 through the valved drain conduit 206, and the pressure is reduced to atmospheric pressure. The door 136 is then opened and the trays 144 or 146 and processed containers therein are then removed from the tunnel 140 and the pressure vessel through the open door.

The next trays of containers to be processed are then loaded into the tunnel 140, the door 136 is closed, and the vessel is raised to about 20 psig by air from air conduit 182. During cooling, the hot water previously stored in the annular chamber 200 has been reduced in temperature below its boiling point at atmospheric pressure. The valved suction conduit 194 and inlet conduit 196 are then opened and the pump 192 is started to repeat the process as above described.

One alternate method of operating the vertically oriented retort system 20b is to drain the hot water through conduit 206 rather than storing the hot water as above described. Another alternate method is to pump the hot water into a separate external storage tank (not shown) similar to that disclosed in FIG. 1. If a separate storage tank is used with the vertical retort system 20b, it is apparent that the valved storage inlet conduit 204 will be connected to the separate storage tank rather than to the annular chamber 200. It is also apparent that in the above referred to modified retort system wherein the tunnel is removed for loading and unloading, either a separate water storage tank must be used or the hot water must be drained from the system.

A modified water heating device 210 is illustrated in FIG. 7 and is intended to be substituted in the retort system 20b in place of the valved steam conduit 188 and perforated annular distribution pipe 190. In the FIG. 7 embodiment, a steam injector 212 introduces steam directly into the valved suction conduit 194' for circulation through the system by the pump 192' as above described.

Although a single steam injector 212 has been illustrated as being in the suction conduit 194' in FIG. 7, it will be understood that one or more steam injectors may be disposed at other locations in the fluid control and circulation system 180. For example, steam injectors may be inserted into the conduits 108 and 110 (FIG. 1) or in the conduit 196 (FIG. 5). Although a cooking temperature of about 250° F. and an overriding air pressure of about 20 psig has been given as operating conditions, it will be understood that it is within the scope of the invention to use other temperatures and pressures since different products require different operating conditions.

From the foregoing description it is apparent that both the horizontally and vertically disposed types of retort systems are adapted to use a minimum amount of heat treatment liquid in excess of that required to fill the tunnel. The containers are heat treated by completely submerging the containers in a liquid within a tunnel and then circulating hot liquid at superatmospheric pressure and temperature through the tunnel and past the product; and thereafter circulating cold water through the tunnel and past the containers to cool the containers and their contents below the boiling point of the liquid at atmospheric pressure. Each type of retort system is capable of storing and reusing the heated cooking liquid for processing the next batch of containers thereby reducing the cost of heating the liquid; or alternately, each type of retort system is capable of being operated without a hot water storage tank thus reducing the initial cost of the apparatus.

Although the best mode contemplated for carrying out the present invention has been herein shown and described, it will be apparent that modification and variations may be made without departing from what is regarded to be the subject matter of the invention.

I claim:

1. In a low liquid volume retort system including means defining a pressure vessel, closure means for selectively opening and closing said pressure vessel for loading and unloading containers therefrom, means defining a tunnel in said pressure vessel having an inlet end and an outlet end and within which the containers are supported during heat treatment, means for circulating at least a container heating heat treatment liquid from the inlet end to and through the outlet end of said tunnel, and means for introducing a gaseous medium into said pressure vessel for maintaining a superatmospheric pressure therein; the improvement which comprises overflow means at the outlet end of said tunnel having an overflow edge over which at least the container heating liquid in the tunnel is discharged, said overflow edge being disposed above the level of the uppermost containers in said tunnel for completely submerging all containers, and means for collecting the overflowing container heating liquid in a shallow pool in the bottom of said vessel and externally of said tunnel for recirculation through said tunnel.

2. An apparatus according to claim 1 wherein said tunnel is disposed horizontally and wherein said shallow pool of liquid is disposed below said tunnel.

3. An apparatus according to claim 2 wherein said liquid is heated while in said pool during a sterilizing cycle of operation and prior to being recirculated through said tunnel.

4. An apparatus according to claim 1 and additionally comprising steam injector means disposed in said recirculating means for reheating the recirculated liquid to processing temperature prior to its re-entry into said tunnel.

5. An apparatus according to claim 2 wherein said tunnel is formed by at least one cart filled with nesting trays having the containers supported therein, said pressure vessel having a water inlet passage therein, means defining an outlet opening for said water inlet passage, resilient sealing means disposed between the periphery of said opening and the periphery of the inlet end of said tunnel, clamping means in said pressure chamber for compressing said sealing means and firmly clamping the periphery of the inlet end of said tunnel means of said cart in fluid tight engagement against said inlet passage.

6. An apparatus according to claim 5 wherein said tunnel includes a plurality of carts, each cart having end frames with flow passages therein, and resilient sealing means on at least one end frame of each cart for peripherally sealing the carts to each other in fluid tight engagement upon actuation of said clamping means.

7. An apparatus according to claim 2 and additionally including fluid flow and circulating control means for first circulating the heating liquid at a predetermined temperature through said tunnel during a heating cycle and thereafter circulating a cooling liquid through said tunnel during a cooling cycle, means defining a hot liquid storage tank, said fluid flow and circulating control means including means for directing and storing only said hot liquid from said shallow pool and tunnel in said storage tank means after said heatint cycle has been completed and during said cooling cycle.

8. In a low liquid volume retort system including means defining a pressure vessel, closure means for selectively opening and closing said pressure vessel for loading and unloading containers therefrom, means defining a tunnel in said pressure vessel having an inlet end and an outlet end and within which the containers are supported during heat treatment, means for circulating at least a container heating heat treatment liquid from the inlet end to and through the outlet end of said tunnel, and means for introducing a gaseous medium into said pressure vessel for maintaining a superatmospheric pressure therein; the improvement which comprises overflow means at the outlet end of said tunnel having an overflow edge over which the container heating liquid in the tunnel is discharged, said tunnel being oriented vertically, means connecting the open inlet end of said tunnel in fluid tight engagement to the lower end of said pressure vessel during circulating of said liquid, said tunnel including vertical walls spaced from and defining an annular substantially liquid tight storage space between said tunnel and said pressure vessel, said overflow edge being disposed above the level of the uppermost containers in said tunnel, said overflowing liquid being received in a shallow pool in the lower portion of said annular space during circulation of a container heating liquid.

9. An apparatus according to claim 8 wherein said tunnel is both sealed in fluid tight engagement and is rigidly secured to said lower end of said pressure vessel.

10. An apparatus according to claim 8 wherein said tunnel is removable from said vessel when said door means is opened for ease in loading and unloading containers from said tunnel and from said pressure vessel.

11. An apparatus according to claim 8 and additionally comprising fluid flow and circulating control means for first circulating a liquid at a predetermined temperature through said tunnel during a heating cycle and thereafter directing a cooling liquid into said tunnel during a cooling cycle, means defining a hot liquid storage tank, said fluid flow and circulating means including means for removing hot liquid from said tunnel and for directing and storing said hot liquid in said storage tank means after said heating cycle has been completed and during said cooling cycle.

12. An apparatus according to claim 11 wherein said storage tank means is said annular storage space.

13. An apparatus according to claim 11 wherein said storage tank means is a pressure tank disposed externally of said vessel and is of sufficient capacity to store only the hot liquid from the shallow pool and from the tunnel.

* * * * *